(12) United States Patent
Kurse et al.

(10) Patent No.: US 8,197,413 B2
(45) Date of Patent: Jun. 12, 2012

(54) TRANSDUCERS, DEVICES AND SYSTEMS CONTAINING THE TRANSDUCERS, AND METHODS OF MANUFACTURE

(75) Inventors: Ravi Kurse, Fremont, CA (US); Marc Stepkowski, Fremont, CA (US); John D. Marshall, Los Gatos, CA (US); Dushyant Shah, San Ramon, CA (US); Derrik Zimmerman, Dublin, CA (US); Joe Carioggia, San Jose, CA (US); Lewis Thomas, Palo Alto, CA (US); Peter Thornton, Los Altos, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 454 days.

(21) Appl. No.: 12/476,126

(22) Filed: Jun. 1, 2009

(65) Prior Publication Data

US 2009/0306518 A1 Dec. 10, 2009

Related U.S. Application Data

(60) Provisional application No. 61/059,431, filed on Jun. 6, 2008.

(51) Int. Cl.
*A61B 8/14* (2006.01)
*H04R 31/00* (2006.01)
(52) U.S. Cl. ............................. 600/466; 600/459; 29/594
(58) Field of Classification Search .................. 600/437, 600/459, 466; 29/594
See application file for complete search history.

(56) References Cited

U.S. PATENT DOCUMENTS

| | | | |
|---|---|---|---|
| 5,131,397 A | 7/1992 | Crowley | |
| 5,186,177 A | 2/1993 | O'Donnell et al. | |
| 5,190,046 A | 3/1993 | Shturman | |
| 5,271,402 A | 12/1993 | Yeung et al. | |
| 5,291,090 A | 3/1994 | Dias | |
| 5,295,958 A | 3/1994 | Shturman | |
| 5,325,860 A | 7/1994 | Seward et al. | |
| 5,331,947 A | 7/1994 | Shturman | |
| 5,377,685 A | 1/1995 | Kazi et al. | |
| 5,453,575 A | 9/1995 | O'Donnell et al. | |
| 5,454,373 A | 10/1995 | Koger et al. | |
| 5,464,016 A | 11/1995 | Nicholas et al. | |
| 5,485,845 A | 1/1996 | Verdonk et al. | |
| 5,590,659 A | 1/1997 | Hamilton et al. | |
| 5,605,155 A | 2/1997 | Chalana et al. | |
| 5,606,975 A | 3/1997 | Liang et al. | |
| 5,640,961 A | 6/1997 | Verdonk | |
| 5,699,806 A | 12/1997 | Webb et al. | |
| 5,724,978 A | 3/1998 | Tenhoff | |
| 5,771,895 A | 6/1998 | Slager | |
| 5,857,974 A | 1/1999 | Eberle et al. | |

(Continued)

FOREIGN PATENT DOCUMENTS

EP 1435835 2/2009

(Continued)

*Primary Examiner* — Michael Rozanski
(74) *Attorney, Agent, or Firm* — Frommer Lawrence & Haug LLP; Bruce E. Black

(57) ABSTRACT

A catheter assembly for an intravascular ultrasound system includes a catheter and an imaging core. The catheter includes a lumen extending along the longitudinal length of the catheter from the proximal end to the distal end and the imaging core is configured and arranged for inserting into the lumen. The imaging core includes a rotatable driveshaft, at least one transducer mounted to the distal end of the rotatable driveshaft, and a twisted wire cable coupled to the at least one transducer. In addition, a number of different transducer arrangements and methods of making transducers are presented.

23 Claims, 11 Drawing Sheets

U.S. PATENT DOCUMENTS

| | | |
|---|---|---|
| 5,876,343 A | 3/1999 | Teo |
| 5,885,218 A | 3/1999 | Teo et al. |
| 5,921,934 A | 7/1999 | Teo |
| 5,947,905 A | 9/1999 | Hadjicostis et al. |
| 5,984,871 A | 11/1999 | TenHoff et al. |
| 5,993,393 A | 11/1999 | Ryan et al. |
| 6,001,062 A | 12/1999 | Masters |
| 6,013,033 A | 1/2000 | Berger et al. |
| 6,019,724 A | 2/2000 | Gronningsaeter et al. |
| 6,019,725 A | 2/2000 | Vesely et al. |
| 6,019,726 A | 2/2000 | Webb |
| 6,027,460 A | 2/2000 | Shturman |
| 6,063,032 A | 5/2000 | Grunwald |
| 6,080,109 A | 6/2000 | Baker et al. |
| 6,106,474 A | 8/2000 | Koger et al. |
| 6,110,121 A | 8/2000 | Lenker |
| 6,149,596 A | 11/2000 | Bancroft |
| 6,165,128 A | 12/2000 | Cespedes et al. |
| 6,213,950 B1 | 4/2001 | Cespedes et al. |
| 6,251,078 B1 | 6/2001 | Moore et al. |
| 6,361,500 B1 | 3/2002 | Masters |
| 6,371,915 B1 | 4/2002 | Koger et al. |
| 6,457,365 B1 | 10/2002 | Stephens et al. |
| 6,499,348 B1 | 12/2002 | Mamayek |
| 6,508,768 B1 | 1/2003 | Hall et al. |
| 6,520,975 B2 | 2/2003 | Branco |
| 6,540,677 B1 | 4/2003 | Angelsen et al. |
| 6,554,801 B1 | 4/2003 | Steward et al. |
| 6,592,520 B1 | 7/2003 | Peszynski et al. |
| 6,641,534 B2 | 11/2003 | Smith et al. |
| 6,645,195 B1 | 11/2003 | Bhat et al. |
| 6,673,015 B1 | 1/2004 | Glover et al. |
| 6,679,845 B2 | 1/2004 | Ritter et al. |
| 6,945,938 B2 | 9/2005 | Grunwald |
| 6,949,072 B2 | 9/2005 | Furnish et al. |
| 7,024,025 B2 | 4/2006 | Sathyanarayana |
| 7,115,092 B2 | 10/2006 | Park et al. |
| 7,187,964 B2 | 3/2007 | Khoury |
| 7,211,045 B2 | 5/2007 | Dala-Krishna et al. |
| 7,226,417 B1 | 6/2007 | Eberle et al. |
| 7,246,959 B2 | 7/2007 | Nakatani |
| 7,297,116 B2 | 11/2007 | Varghese et al. |
| 7,306,561 B2 | 12/2007 | Sathyanarayana |
| 7,314,448 B2 | 1/2008 | Barbato et al. |
| 7,374,538 B2 | 5/2008 | Nightingale et al. |
| 7,578,790 B2 | 8/2009 | Sathyanarayana |
| 2002/0022782 A1 | 2/2002 | Kiepen et al. |
| 2002/0102216 A1 | 8/2002 | Lanza et al. |
| 2003/0120204 A1 | 6/2003 | Unger et al. |
| 2003/0225336 A1 | 12/2003 | Callister et al. |
| 2004/0015079 A1 | 1/2004 | Berger et al. |
| 2004/0039286 A1 | 2/2004 | Kuban et al. |
| 2004/0230116 A1 | 11/2004 | Cowan et al. |
| 2005/0075584 A1 | 4/2005 | Cali |
| 2005/0137478 A1 | 6/2005 | Younge et al. |
| 2005/0154315 A1 | 7/2005 | Nair et al. |
| 2005/0203410 A1 | 9/2005 | Jenkins |
| 2006/0030777 A1 | 2/2006 | Liang et al. |
| 2006/0036146 A1 | 2/2006 | Sathyanarayana |
| 2006/0036147 A1 | 2/2006 | Sathyanarayana |
| 2006/0084875 A1 | 4/2006 | Knight |
| 2006/0100522 A1 | 5/2006 | Yuan et al. |
| 2006/0106320 A1 | 5/2006 | Barbato |
| 2006/0106375 A1 | 5/2006 | Werneth et al. |
| 2006/0173350 A1 | 8/2006 | Yuan et al. |
| 2006/0237652 A1 | 10/2006 | Kimchy et al. |
| 2006/0253028 A1 | 11/2006 | Lam et al. |
| 2007/0013269 A1 | 1/2007 | Huang |
| 2007/0016054 A1 | 1/2007 | Cao et al. |
| 2007/0038111 A1 | 2/2007 | Rehrig et al. |
| 2007/0066900 A1 | 3/2007 | O'Keeffe |
| 2007/0106155 A1 | 5/2007 | Goodnow et al. |
| 2007/0129625 A1 | 6/2007 | Li et al. |
| 2007/0167801 A1 | 7/2007 | Webler et al. |
| 2007/0167827 A1 | 7/2007 | Masters |
| 2007/0178767 A1 | 8/2007 | Harshman et al. |
| 2007/0232882 A1 | 10/2007 | Glossop et al. |
| 2007/0282202 A1 | 12/2007 | Maurice et al. |
| 2008/0004527 A1 | 1/2008 | Coleman et al. |
| 2008/0009745 A1 | 1/2008 | Hossack et al. |
| 2008/0091104 A1 | 4/2008 | Abraham |
| 2008/0097217 A1 | 4/2008 | Itoh et al. |
| 2008/0097403 A1 | 4/2008 | Donaldson et al. |
| 2008/0123911 A1 | 5/2008 | Lam et al. |
| 2008/0154136 A1 | 6/2008 | Webler |
| 2008/0161696 A1 | 7/2008 | Schmitt et al. |
| 2008/0167560 A1 | 7/2008 | Thornton |
| 2008/0200815 A1 | 8/2008 | Van Der Steen et al. |
| 2009/0001853 A1 | 1/2009 | Adachi et al. |
| 2009/0005675 A1 | 1/2009 | Grunwald et al. |
| 2009/0043198 A1 | 2/2009 | Milner et al. |
| 2009/0051250 A1 | 2/2009 | Shah et al. |
| 2009/0171216 A1 | 7/2009 | Sadaka |

FOREIGN PATENT DOCUMENTS

| | | |
|---|---|---|
| WO | WO-94/07418 | 4/1994 |
| WO | WO-94/23652 | 10/1994 |
| WO | WO-97/09924 | 3/1997 |
| WO | WO-98/24065 | 6/1998 |
| WO | WO-98/48885 | 11/1998 |
| WO | WO-99/39697 | 8/1999 |
| WO | WO-00/24318 | 5/2000 |
| WO | WO-2004/021044 | 3/2004 |
| WO | WO-2005/013822 | 2/2005 |
| WO | WO-2005/099583 | 10/2005 |
| WO | WO-2006/061829 | 6/2006 |
| WO | WO-2007/084981 | 7/2007 |
| WO | WO-2008/054395 | 5/2008 |
| WO | WO-2008/100386 | 8/2008 |
| WO | WO-2009/023626 | 2/2009 |

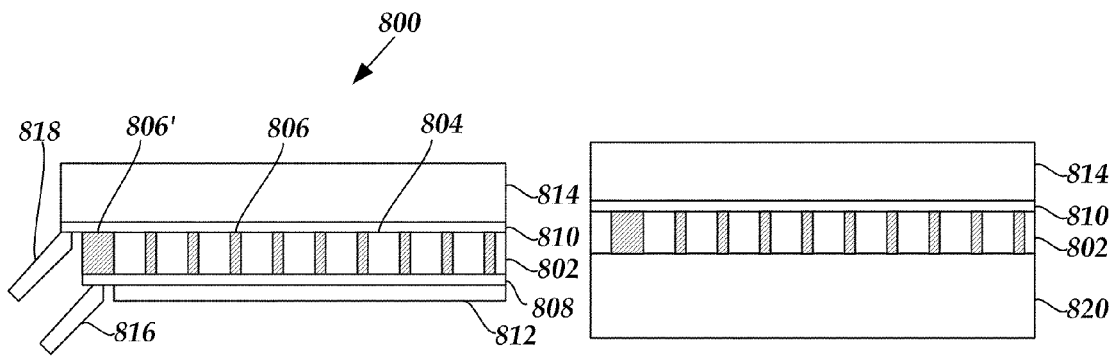
Fig. 12
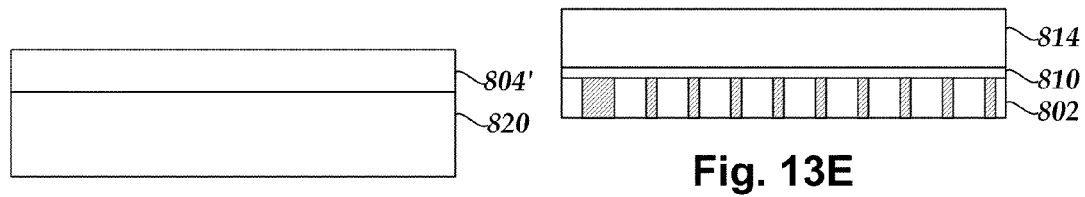
Fig. 13A
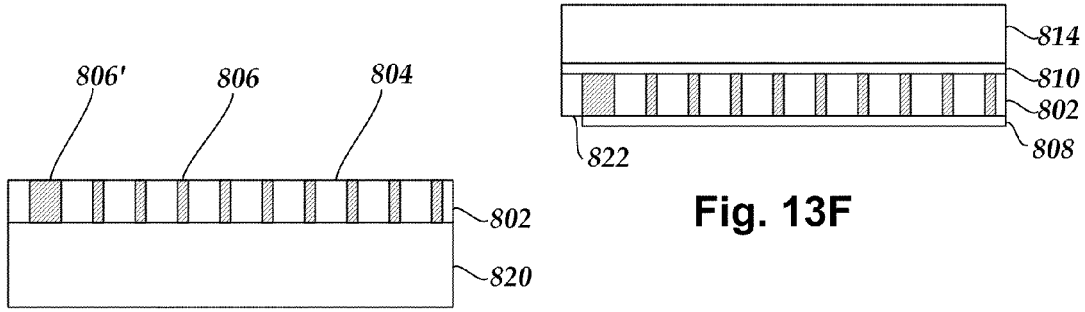
Fig. 13B
Fig. 13C
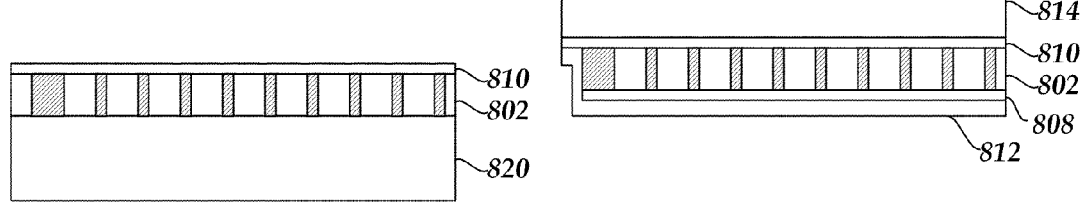
Fig. 13D
Fig. 13E
Fig. 13F
Fig. 13G

TRANSDUCERS, DEVICES AND SYSTEMS CONTAINING THE TRANSDUCERS, AND METHODS OF MANUFACTURE

CROSS REFERENCE TO RELATED APPLICATION

This application claims priority of U.S. Provisional Patent Application Ser. No. 61/059,431, filed on Jun. 6, 2008, the entire contents of which is hereby incorporated by reference.

TECHNICAL FIELD

The present invention is directed to the area of transducers for ultrasound imaging systems, devices and systems containing the transducers, and methods of making and using the transducers. The present invention is also directed to transducers for an intravascular ultrasound imaging system.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

One embodiment is an ultrasound transducer that includes a transducer element comprising a material configured and arranged to convert electrical energy to ultrasound energy. The transducer element further comprises a first non-transducing pad defined in the transducer element. The ultrasound transducer also includes a first metal layer substantially disposed over a first surface of the transducer element and over the first non-transducing pad; and a second metal layer substantially disposed over a second surface of the transducer element.

Another embodiment is an ultrasound transducer that includes a transducer element comprising a material configured and arranged to convert electrical energy to ultrasound energy; a first metal layer substantially disposed over a first surface of the transducer element; a second metal layer substantially disposed over a second surface of the transducer element (the second surface opposing the first surface); a backing layer disposed over the second metal layer; and a third metal layer disposed over the backing layer. The third metal layer defines a first contact and a second contact that are separated from each other. The first contact is coupled to the first metal layer by a first contact via and the second contact is coupled to the second metal layer by a second contact via.

Yet another embodiment is an ultrasound transducer that includes a transducer element comprising a material configured and arranged to convert electrical energy to ultrasound energy. The ultrasound transducer further includes a first thin film circuit comprising a first substrate with metal traces disposed on opposing sides of the first substrate and electrically coupled together. The metal traces are configured and arranged to provide a contact pad on one side of the first substrate and an electrode for providing electrical signals to the transducer element on another side of the first substrate. The ultrasound transducer also includes a second thin film circuit comprising a second substrate with metal traces disposed on opposing sides of the second substrate and electrically coupled together. The metal traces are configured and arranged to provide a contact pad on one side of the second substrate and an electrode for providing electrical signals to the transducer element on another side of the second substrate. The transducer element is disposed between the first and second thin film circuits.

A further embodiment is an ultrasound transducer that includes a transducer element comprising a material configured and arranged to convert electrical energy to ultrasound energy; a carrier substrate comprising a first surface and a second surface opposing the first surface; a first metal layer disposed on the first surface of the carrier substrate and defining a first contact and a second contact that are separate from each other; a second metal layer disposed on the second surface of the carrier substrate and in electrical communication with the second contact on the first surface of the carrier substrate; a third metal layer; and a conducting structure electrically coupling the first contact with the third metal layer. The transducer element is disposed between the second metal layer and the first metal layer. The conducting structure itself is electrically insulated from the transducer element.

Another embodiment is an ultrasound transducer that includes a transducer element comprising a material configured and arranged to convert electrical energy to ultrasound energy. The transducer element has a first surface, a second surface opposing the first surface, and an edge surface between the first and second surfaces. The ultrasound transducer further includes a first metal layer disposed over the first surface of the transducer element; a second metal layer disposed over the second surface of the transducer element; a first contact extending from the first metal layer along a first portion of the edge surface of the transducer element; and a second contact extending from the first metal layer along a second portion of the edge surface of the transducer element.

Yet another embodiment is a method of making an ultrasound transducer including forming at least one first vertical slot extending from a first surface partway through a transducer element. Metal is disposed within the first vertical slot(s) to at least coat exposed surfaces of the transducer element within the first vertical slot(s). A first metal layer is disposed over the first surface of the transducer element and in contact with the metal disposed within the first vertical slot(s). At least one second vertical slot is formed extending from a second surface partway through the transducer element. The second surface of the transducer element opposes the first surface of the transducer element. Metal is disposed within the second vertical slot(s) to at least coat exposed surfaces of the transducer element within the second vertical slot(s). A second metal layer is disposed over the second surface of the transducer element and in contact with the metal disposed within the second vertical slot(s). The transducer element is cut through the first and second vertical slots to form an ultrasound transducer with first and second contacts formed from the metal disposed in the first and second vertical slots, respectively.

A further embodiment is a catheter assembly for an intravascular ultrasound system that includes a catheter and an imaging core. The catheter has a longitudinal length, a distal end, and a proximal end. The catheter also includes a lumen extending along the longitudinal length of the catheter from the proximal end to the distal end. The imaging core is configured and arranged for inserting into the lumen. The imaging core includes a rotatable driveshaft having a distal end and a longitudinal length, at least one transducer mounted to the distal end of the rotatable driveshaft, and a twisted wire cable. The at least one transducer is configured and arranged for transforming applied electrical pulses to acoustic pulses and also for transforming received echo pulses to electrical pulses. The twisted wire cable includes i) two wires running along the cable and electrically coupled to respective contacts of the at least one transducer, and ii) a shield extending along the cable and within which a portion of the two wires are disposed.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 12 is a schematic cross-sectional view of a fourth embodiment of a transducer, according to the invention;

FIGS. 13A-13G are schematic cross-sectional views of steps in one embodiment of a method of making the transducer of FIG. 12, according to the invention;

DETAILED DESCRIPTION

The present invention is directed to the area of transducers for ultrasound imaging systems, devices and systems containing the transducers, and methods of making and using the transducers. The present invention is also directed to transducers for an intravascular ultrasound imaging system.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,246,959; 7,306,561; and 6,945,938; as well as U.S. Patent Application Publication Nos. 20060253028; 20070016054; 20060106320; 20070038111; 20060173350; and 20060100522, all of which are incorporated by reference.

Figure 1:
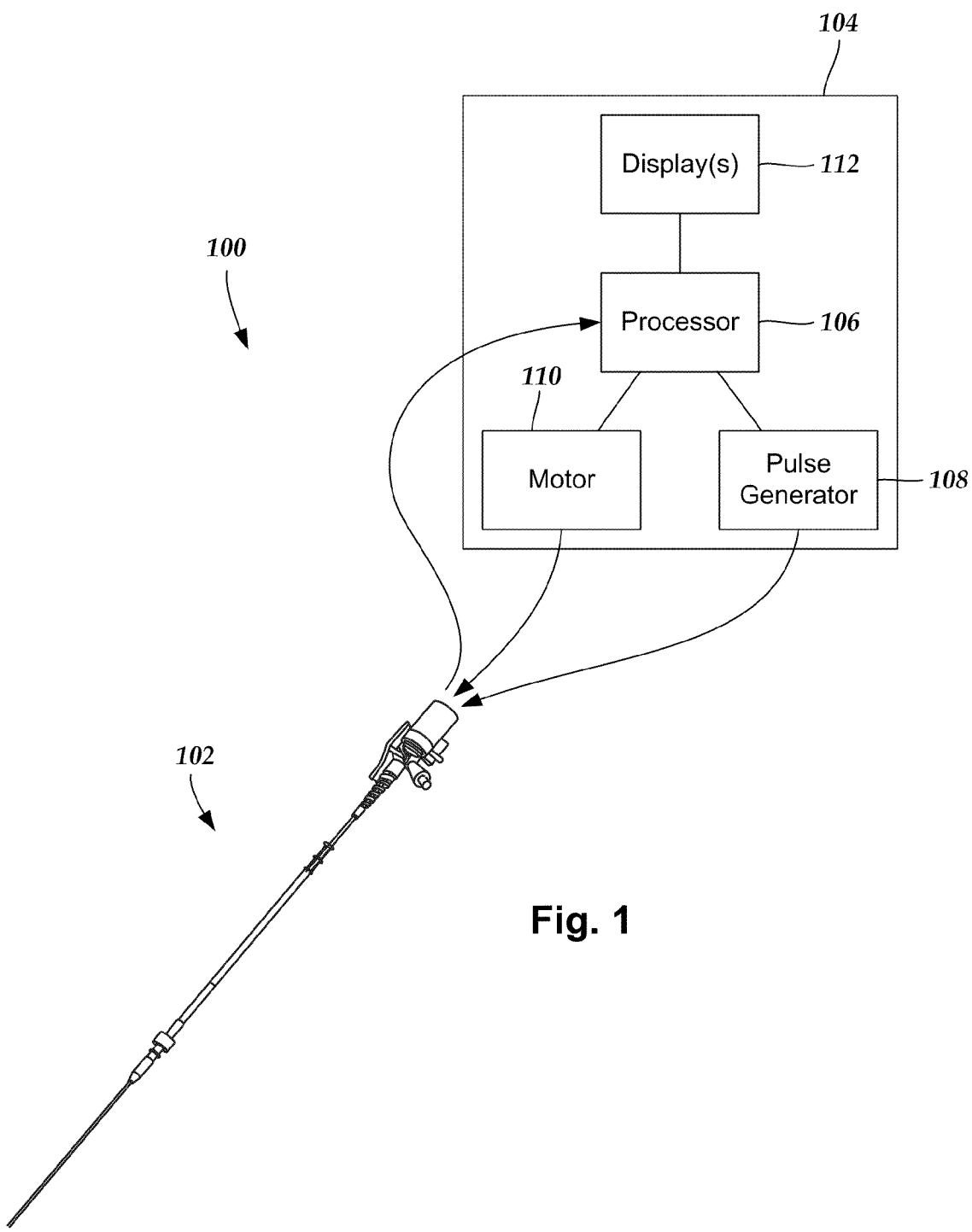
FIG. 1 is a schematic view of one embodiment of an intravascular ultrasound imaging system, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a motor 110, and one or more displays 112. In at least some embodiments, the pulse generator 108 forms electric pulses that may be input to one or more transducers (312 in FIG. 3) disposed in the catheter 102.

In at least some embodiments, mechanical energy from the motor 110 may be used to drive an imaging core (306 in FIG. 3) disposed in the catheter 102. In at least some embodiments, electric pulses transmitted from the one or more transducers (312 in FIG. 3) may be input to the processor 106 for processing. In at least some embodiments, the processed electric pulses from the one or more transducers (312 in FIG. 3) may be displayed as one or more images on the one or more displays 112. In at least some embodiments, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the motor 110, the velocity or length of the pullback of the imaging core (306 in FIG. 3) by the motor 110, or one or more properties of one or more images formed on the one or more displays 112. In some embodiments, the parts of the control module 104 (i.e., the processor 106, the pulse generator 108, the motor 110, and the one or more displays 112) may be in one unit. In other embodiments, the parts of the control module 104 are in two or more units.

Figure 2:
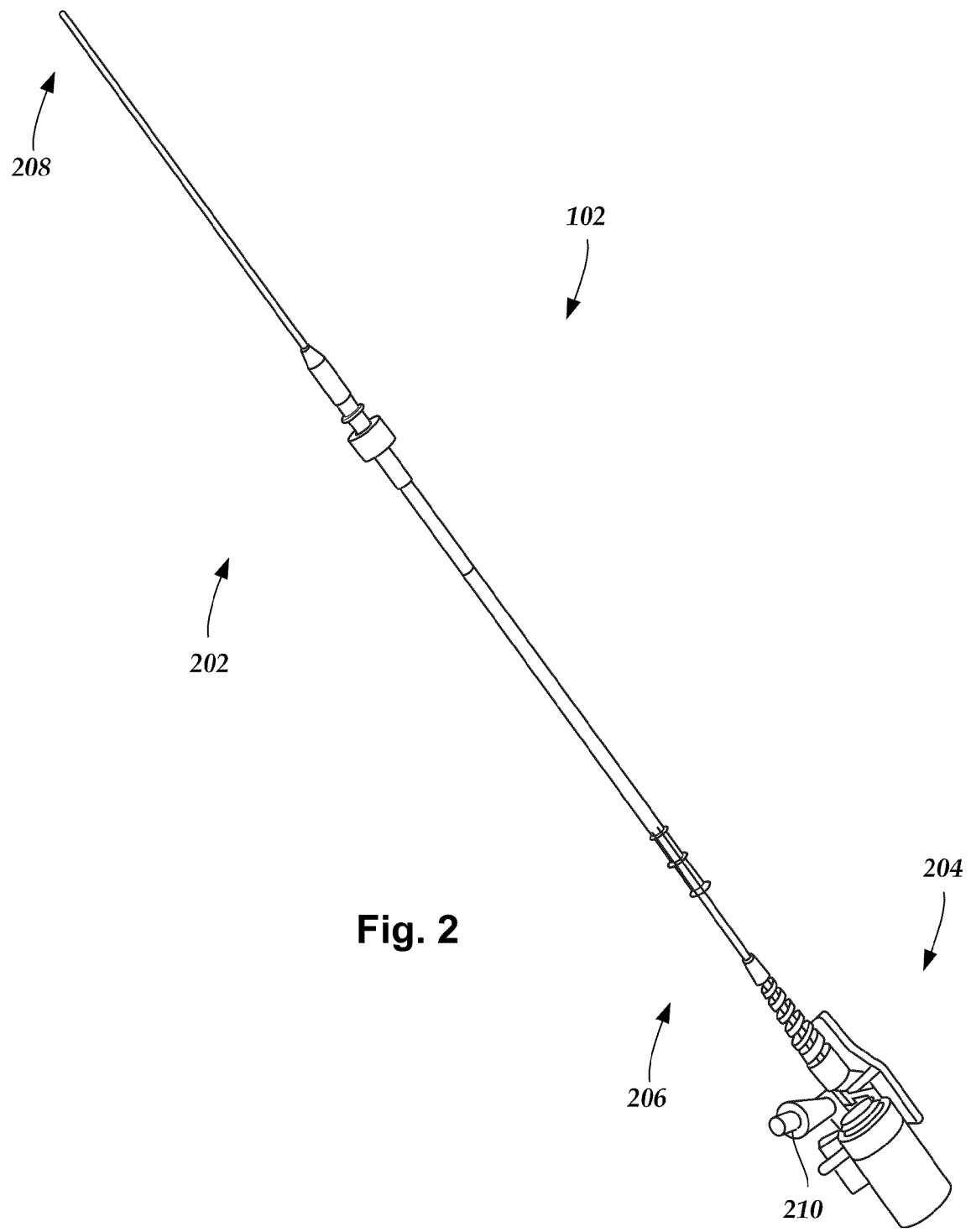
FIG. 2 is a schematic side view of one embodiment of a catheter of an intravascular ultrasound imaging system, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. In at least some embodiments, the catheter 102 defines at least one flush port, such as flush port 210. In at least some embodiments, the flush port 210 is defined in the hub 204. In at least some embodiments, the hub 204 is configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
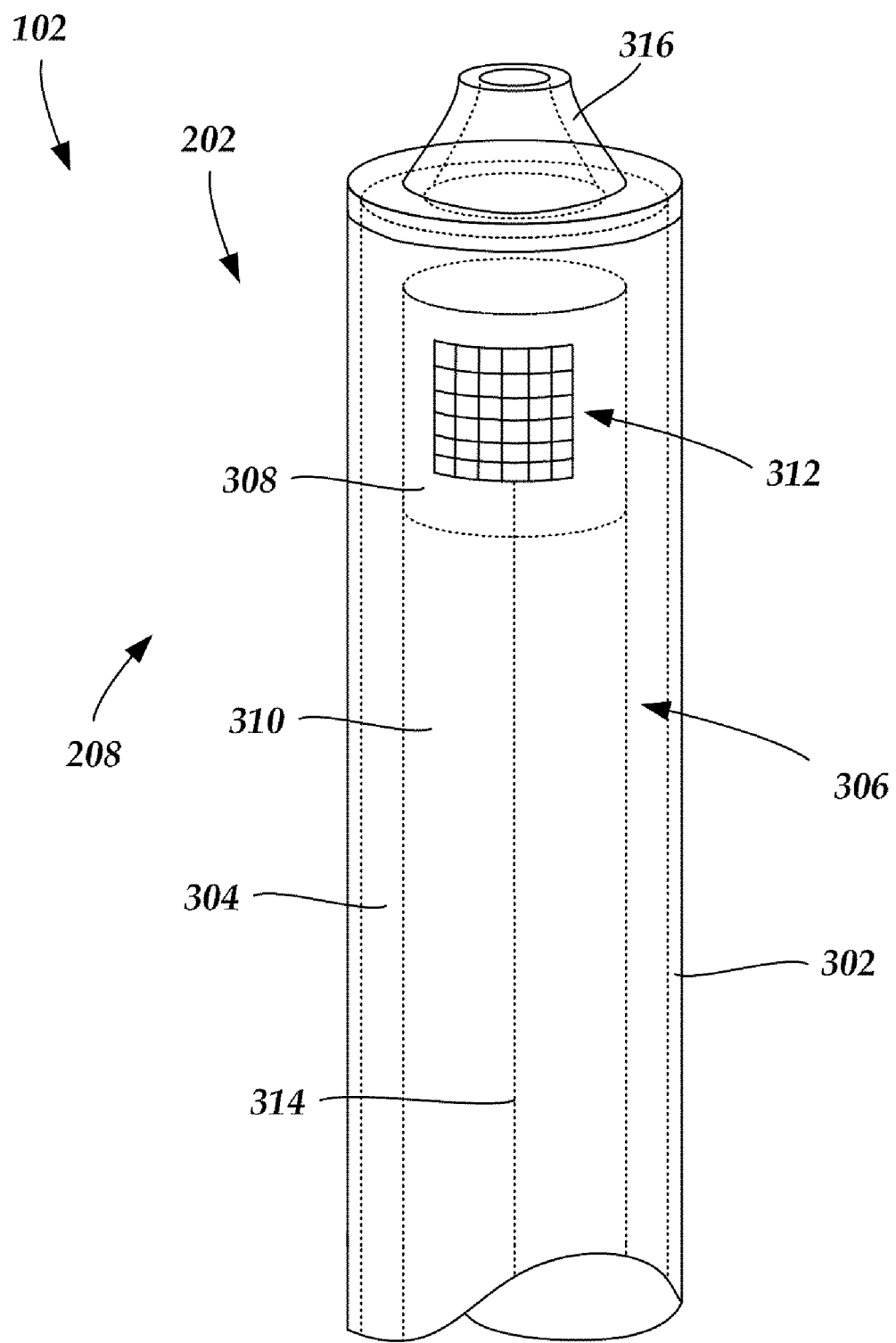
FIG. 3 is a schematic perspective view of one embodiment of a distal end of an elongated member of the catheter shown in FIG. 2 with an imaging core disposed in a lumen in the distal end of the elongated member, according to the invention.

FIG. 3 is a schematic perspective view of one embodiment of the distal end 208 of the elongated member 202 of the catheter 102. The elongated member 202 includes a sheath 302 and a lumen 304. An imaging core 306 is disposed in the lumen 304. The imaging core 306 includes an imaging device 308 coupled to a distal end of a rotatable driveshaft 310.

The sheath 302 may be formed from any flexible, biocompatible material suitable for insertion into a patient. Examples of suitable materials include, for example, polyethylene, polyurethane, polytetrafluoroethylene (PTFE), other plastics, and the like or combinations thereof.

One or more transducers 312 may be mounted to the imaging device 308 and employed to transmit and receive acoustic pulses. In a preferred embodiment (as shown in FIG. 3), an array of transducers 312 are mounted to the imaging device 308. In other embodiments, a single transducer may be employed. In yet other embodiments, multiple transducers in an irregular-array may be employed. Any number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, lead magnesium niobate-lead titanates, and the like. These materials will be collectively referred to as "piezoelectric materials". Additionally, capacitive micromachined ultrasound transducers (CMUTs) or the like may be used.

Pressure distortions on the surface of the one or more transducers 312 can be generated in order to form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency or frequencies in one or more selected directions. For example, transducers may be disc-shaped, block-shaped, ring-shaped, layered, and the like. The one or more transducers may be formed in the desired shape by any process including, for example, dicing, machining, dice and fill, chemical etching, plasma etching, reactive ion etching, microfabrication, and the like.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

In at least some embodiments, the imaging core 306 may be rotated about a longitudinal axis of the catheter 102. As the imaging core 306 rotates, the one or more transducers 312 emit acoustic pulses in different radial directions. When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In at least some embodiments, the rotation of the imaging core 306 is driven by the motor 110 disposed in the control module (104 in FIG. 1).

As the one or more transducers 312 rotate about the longitudinal axis of the catheter 102 emitting acoustic pulses, a plurality of images are formed that collectively generate a radial cross-sectional image of a portion of the region surrounding the one or more transducers 312, such as the walls of a blood vessel of interest and the tissue surrounding the blood vessel. In at least some embodiments, the radial cross-sectional image can be displayed on one or more displays 112.

In at least some embodiments, the imaging core 306 may also move longitudinally along the blood vessel within which the catheter 102 is inserted so that a plurality of cross-sectional images may be formed along a longitudinal length of the blood vessel. In at least some embodiments, during an imaging procedure the one or more transducers 312 may be retracted (i.e., pulled back) along the longitudinal length of the catheter 102. In at least some embodiments, the motor 110 drives the pullback of the imaging core 306 within the catheter 102. In at least some embodiments, the motor 110 pullback distance of the imaging core is at least 5 cm. In at least some embodiments, the motor 110 pullback distance of the imaging core is at least 10 cm. In at least some embodiments, the motor 110 pullback distance of the imaging core is at least 15 cm. In at least some embodiments, the motor 110 pullback distance of the imaging core is at least 20 cm. In at least some embodiments, the motor 110 pullback distance of the imaging core is at least 25 cm.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 1 MHz to 60 MHz.

In at least some embodiments, one or more conductors 314 electrically couple the transducers 312 to the control module 104 (See FIG. 1). In at least some embodiments, the one or more conductors 314 extend along a longitudinal length of the rotatable driveshaft 310.

In at least some embodiments, the catheter 102 with one or more transducers 312 mounted to the distal end 208 of the imaging core 308 may be inserted percutaneously into a patient via an accessible blood vessel, such as the femoral artery, at a site remote from the selected portion of the selected region, such as a blood vessel, to be imaged. The catheter 102 may then be advanced through the blood vessels of the patient to the selected imaging site, such as a portion of a selected blood vessel.

In many conventional transducer arrangements, the transducer is coupled to the remainder of the system using a coaxial cable. One contact of the transducer is coupled to the conductor that runs through the center of the coaxial cable and the other contact of the transducer is coupled to the cylindrical shield of the coaxial cable. Such an arrangement can lead to an unbalanced electrical connection between the transducer and the other electronic components of the ultrasound system.

Moreover, the connections to the transducer are often made using conductive adhesive to avoid other wire attachment techniques, such as welding and soldering, that would raise the temperature of the heat-sensitive piezoelectric material of the transducer. Conductive adhesives, however, can be unreliable. For example, the adhesives may lose their ability to reliably attach the wires to the transducer when exposed to chemical sterilizing agents, such as ethylene oxide, which are often used to sterilize the ultrasound catheter between uses.

Figure 4:
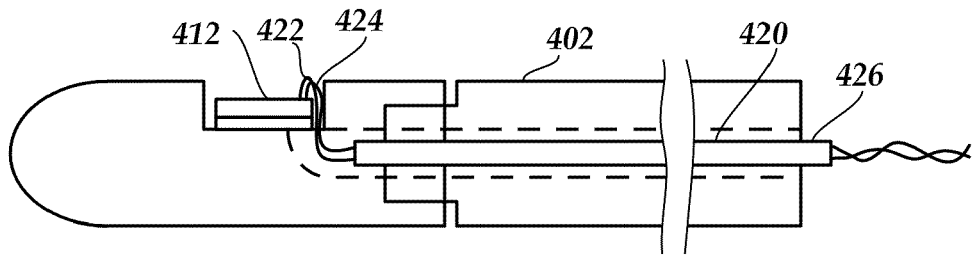
FIG. 4 is schematic side view of one embodiment of a tip of a catheter with a transducer and a twisted pair cable, according to the invention.

FIG. 4 illustrates an alternative arrangement in which the transducer 412, disposed in the catheter 402, is coupled to the remainder of the electronics of the imaging system using a shielded twisted pair cable 420. The shielded twisted pair cable 420 includes two insulated wires 422, 424, that are twisted together along the cable, as well as a metal shield 426 that can be electrically grounded. One of the wires 422 can be coupled to a first contact of the transducer 412 and the other wire 424 can be coupled to a second contact of the transducer. This arrangement provides for a balanced electrical connection with the transducer. The transducer 412 can be any transducer including currently available transducers. The wires 420, 422 can be attached to the transducer using any suitable method including conductive adhesives. As described in more detail below, the transducer can be arranged to allow the wires to be attached using heat-generating techniques, such as welding, soldering, thermal compression bonding, and the like.

Figure 5:
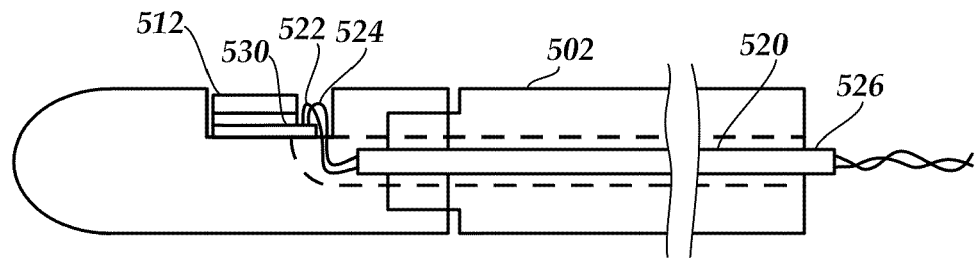
FIG. 5 is a schematic side view of one embodiment of a tip of a catheter with a modular arrangement for attachment of a transducer, according to the invention.

FIG. 5 illustrates another arrangement in which a transducer 512, disposed in a catheter 502, is coupled to a shielded twisted pair cable 520 (with two wires 522, 524 and a conductive shield 526) using a modular fitting 530. In at least some embodiments of this arrangement, the transducer 512 includes contacts (not shown) that couple (e.g., using a conductive adhesive or simply by contact) to corresponding contacts (not shown) on the modular fitting 530. The contacts on the modular fitting 530 are electrically coupled to pads (not shown) to which the wires 522, 524 can be attached. The wires 522, 524 can be attached to the pads of the modular fitting using any suitable technique. In particular, heat-generating techniques can be used for attachment of the wires 522, 524 because the piezoelectric material of the transducer is sufficiently distant that the heat will not damage it. In at least some instances, the wires may be attached to the modular fitting before the transducer is attached to the modular fitting. A modular arrangement, such as that illustrated in FIG. 5, may also allow the transducer 512 to be removed or replaced without detaching the wires of the twisted pair cable 520 from the transducer.

There are a variety of arrangements and methods for forming a transducer. Typically, transducers have a number of different components including a transducer element, made of piezoelectric material or the like, that is disposed between at least two metal layers (or contact layers) through which electrical signals are provided to cause the transducer to emit ultrasound energy. The metal layers also receive electrical signals from the transducer element when the element receives ultrasound signals. The transducer may also optionally include at least one backing layer, and optionally, at least one matching layer.

Any suitable transducer element can be used in the transducers disclosed herein. In general, the transducer element is made of a material, such as a piezoelectric material or the like, that converts electrical signals into ultrasound signals and vice versa. The transducer element, unless otherwise indicated, can be a single crystal transducer element or the transducer element can have one or more individual transducing members optionally separated by non-transducing material (see e.g., FIG. 6) or any other suitable arrangement of transducing members.

The metal layers and contact layers can be formed using any suitable conductive material including metals, alloys, and multi-layer conductive arrangements (e.g., multiple layers of different metals or alloys). Any metal or alloy can be used. For biological applications (e.g., intravascular ultrasound (IVUS) imaging), preferably any exposed portion of the metal or contact layers is made of a material (such as gold, platinum, platinum/iridium alloy, or silver-filled epoxy) that does not corrode when exposed to biological fluids under typical operating conductions. These materials may be plated over other metals, such as copper, Ni/Cr, Ni/Zn, and the like that may otherwise corrode. For example, copper or Ni/Cr can be covered by gold.

The optional matching layer is made of a material that acoustically matches the transducer element to the biological environment. For example, the matching layer may facilitate matching the high acoustic impedance of the transducer element with the lower acoustic impedance of the surroundings, such as tissue and fluids within which the catheter is disposed. Any suitable material may be used including, but not limited to, parylene, epoxy, polyimide, other polymers, and the like.

In some embodiments, the matching layer is non-conductive. In other embodiments, particularly when the matching layer is disposed between the transducer element and a metal layer, the matching layer is conductive. The matching layer can be made conductive by using, for example, a conductive polymer or by including conductive particles (e.g., metal, graphite, or alloy particles) within the polymeric material of the matching layer.

The optional backing layer can be provided for a variety of purposes including, but not limited to, device stability, protection, acoustic matching, or acoustic absorption. The backing layer can be made using any suitable material including, but not limited to, parylene, epoxy, filled epoxies, other polymers, and the like. In some embodiments, the backing layer is non-conductive. In other embodiments, particularly when the backing layer is disposed between the transducer element and a metal layer, the backing layer is conductive. The backing layer can be made conductive by using, for example, a conductive polymer or by including conductive particles (e.g., metal, graphite, or alloy particles) within the polymeric material of the backing layer. Optionally, the backing layer may also function as a matching layer and be formed using a material that acoustically matches the transducer element.

The backing and matching layers may be disposed on other layers of the transducer using any suitable method. Examples of methods for forming the backing and matching layers include, but are not limited to, spin coating, dip coating, spraying, vacuum deposition, chemical deposition, sputtering, casting, and the like or even adhering a pre-made backing or matching layer to another layer using an adhesive.

Figure 6:
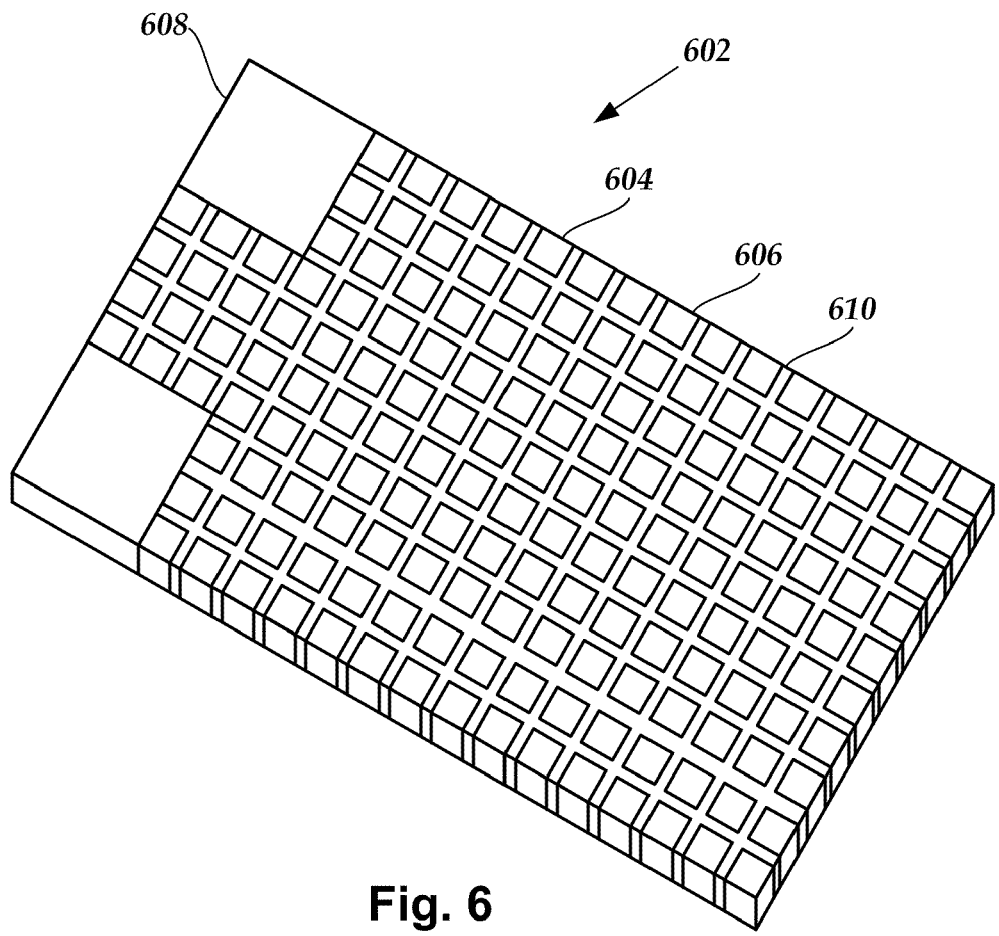
FIG. 6 is a schematic perspective view of one embodiment of a transducer element with non-transducing pads, according to the invention.

FIG. 6 illustrates one embodiment of a transducer element 602 that, when coupled to metal layers as described below, can be used to form a transducer. The transducer element 602 includes piezoelectric material 604 that forms multiple piezoelectric transducing members 606. Each of the transducing members is separated from the others by non-transducing material 610, such as epoxy, polyimide, silicon, alumina, and the like. In at least one embodiment, the transducer element is formed from a slab of piezoelectric material (typically disposed on a carrier) that is etched, scored, sliced, cut, diced, or otherwise separated into the individual transducing members. The non-transducing material may then be disposed between the transducing members using a suitable technique, such as coating methods.

The transducer element 602 also includes at least two non-conductive pads 608. Preferably, these pads are made of a heat-resistant material and, more preferably, are made of a material that does not readily conduct heat. For example, the pads can be made of epoxy, filled epoxy, and the like. For example, a low viscosity epoxy such as Epotek™ 301-2 (Epoxy Technology, Bilerica, Mass.) may be used. The pads 608 may be made of he same material as the non-transducing material 610 and may be formed using the same techniques as are used to dispose the non-transducing material between the transducing members.

These non-conductive pads 608 will be disposed below, or above, metal contact sites, as described in more detail below, so that the wires (see, e.g., wires 422, 424 of FIG. 4) that couple the transducer to the remainder of the imaging system electronics can be attached using, for example, heat-based bonding techniques, such as, for example, laser welding, hot bar solder reflow, thermal compression bonding, gold ball bonding, other soldering or welding techniques, or other techniques that include the application of heat to attach the wires. The non-conductive pads 608 provide protection from heat to the piezoelectric material of the transducing members so that these wire attachment techniques can be used.

Figure 7:
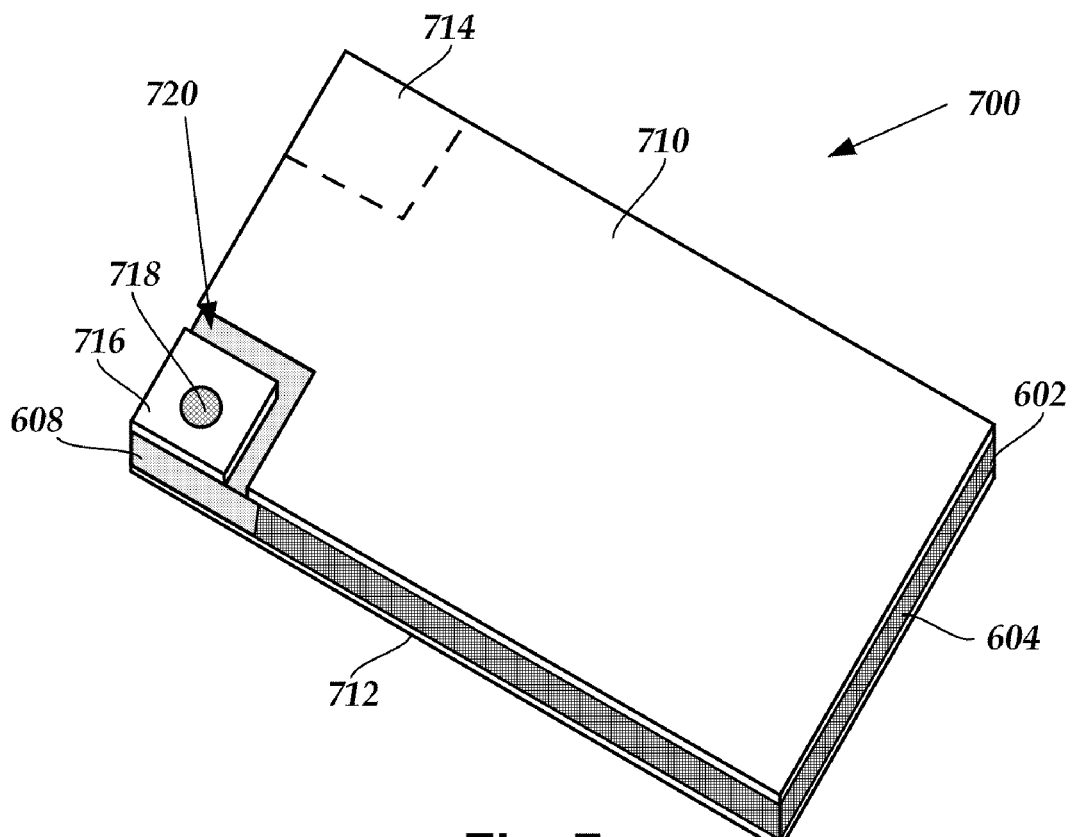
FIG. 7 is a schematic perspective view of one embodiment of a transducer with the transducer element of FIG. 6, according to the invention.

FIG. 7 illustrates one embodiment of a transducer 700 that uses the transducer element 602 of FIG. 6. The transducer element 602 includes the piezoelectric material 604 (formed as individual transducing members as illustrated in FIG. 6, although this detail is not shown in FIG. 7 for purposes of clarity) and the non-conductive pads 608. The transducer 700 includes a top metal layer 710 and a bottom metal layer 712. A metal pad 716 is disposed on the top of the transducer element 602, but is electrically isolated from the top metal layer 710 by a separation 720 (e.g., by the removal of conductive material between the metal pad and the top metal layer.). The metal pad 716 is electrically coupled to the bottom metal layer 712 through a conductive via 718 that is formed by making a hole through at least the pad 608 and plating or filling the hole with metal or another suitable electrically conducting material. The portion 714 of the top metal layer 710 and the metal pad 716 are each disposed over one of the non-conductive pads 608 of the transducer element 602 and provide attachment sites for a wire (see FIG. 4).

The metal layers 710, 712 can be disposed on the transducer element 602 using any suitable method including, but not limited to, electroless plating, electroplating, evaporation, sputtering, chemical or physical vapor deposition, and the like. The separation 720 between the top metal conductive layer 710 and the metal pad 716 can be formed using an suitable technique including patterning a metal layer disposed on the top of the transducer element 602 using a positive or negative photoresist and etching away, or otherwise removing, a portion of that metal layer to form the top metal layer 710 and the metal pad 716 with separation 720. Alternatively, the transducer element 602 may be masked prior to the deposition of the metal so that the separation 720 is formed with the deposition of the metal layer 710 and metal pad 716.

The via 718 can be formed by any suitable method including, but not limited to, drilling, plasma etching, chemical etching, laser ablating, sputter etching, or otherwise making a hole through at least the non-conductive pad 608 of the transducer element. In one embodiment, this hole is formed prior to disposing the top metal layer 710 or bottom metal layer 712 (or both) on the transducer element 602 so that the hole can be coated or filled with metal as the top or bottom metal layer is formed. It will be understood, however, that the hole can be opened and the via 718 coated or filled with metal after the top and bottom metal layers 710, 712 are formed.

Figure 8:
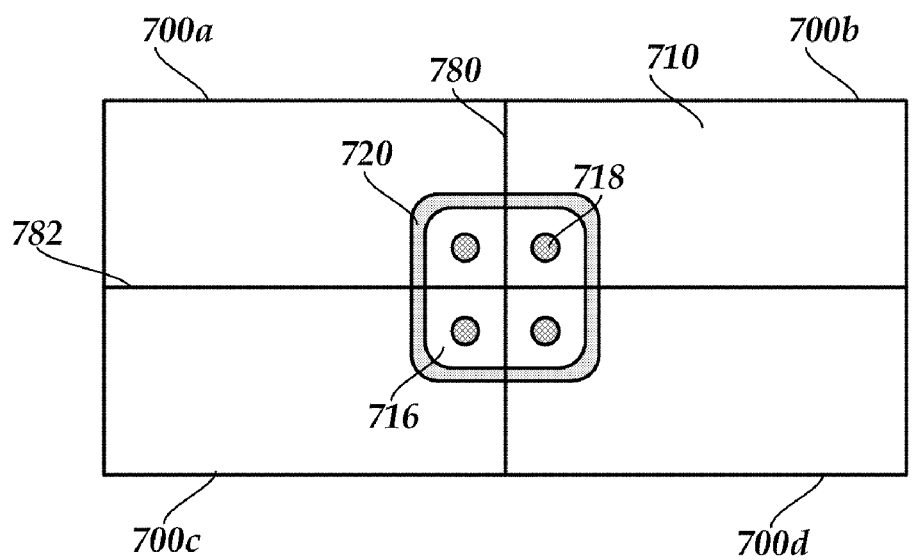
FIG. 8 is a schematic top view of one embodiment of an arrangement containing multiple transducers of FIG. 7, according to the invention.

FIG. 8 illustrates one arrangement in which four transducers 700a, 700b, 700c, and 700d can be formed together and then separated along lines 780, 782. Such an arrangement permits the simultaneous patterning of a metal layer to form the top metal layer 710, metal pad 716, and separation 720 for all four transducers. It will be recognized that this arrangement can be repeated as a larger arrangement to prepare more than four transducers together.

Figure 9:
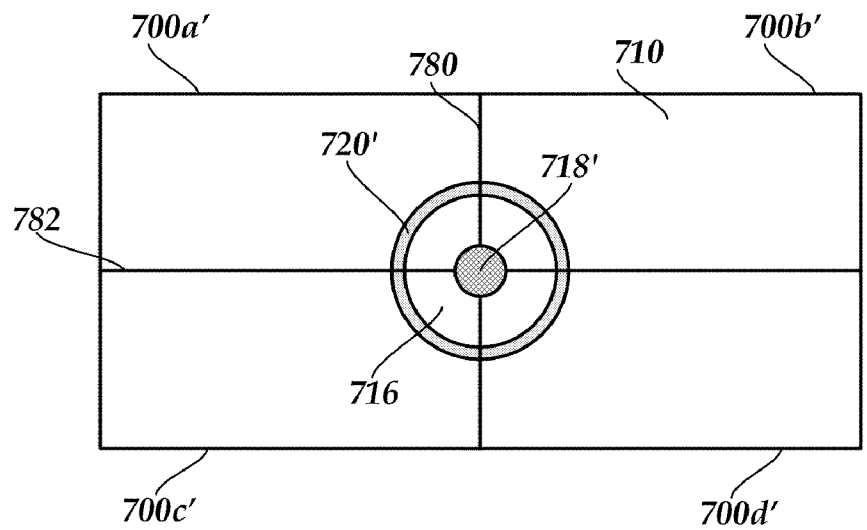
FIG. 9 is a schematic top view of another embodiment of an arrangement containing multiple transducers, according to the invention.
Figure 10:
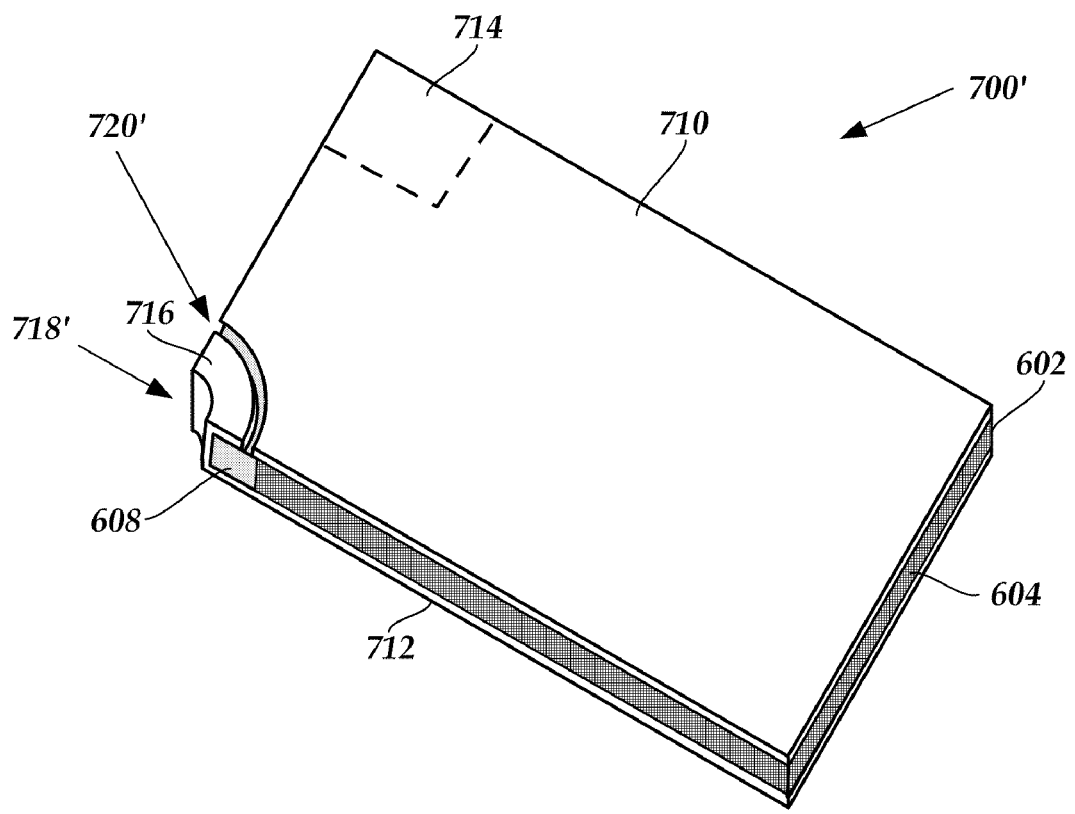
FIG. 10 is a schematic perspective view of one embodiment of a transducer of FIG. 9 with the transducer element of FIG. 6, according to the invention.

FIG. 9 illustrates an alternate arrangement for forming four transducers 700a', 700b', 700c' and 700d'. In this arrangement, instead of four vias, a single via 718' is provided. In addition, the separation 720' between the metal layer 710 and metal pad 716' may be circular, rather than square or rectangular, although it will be understood that in any of the embodiments in FIGS. 7-10, the separation can have any shape as long as the top metal layer 710 and metal pad 716, 716' are not in electrical contact. FIG. 10 illustrates one of the transducers 700' of FIG. 9 with the same elements as the transducer 700 of FIG. 7 except that a portion 718' of the side surface of non-conductive pad 608 is coated with metal to electrically couple the metal pad 716 to the bottom metal conductive layer 712.

Any of the embodiments in FIGS. 7-10 can be bonded to a backing layer (preferably, attached to the bottom metal layer). This backing layer may also be an acoustic matching layer. In addition, an acoustic matching layer may be disposed over at least a portion of the top metal layer.

Figure 11A:
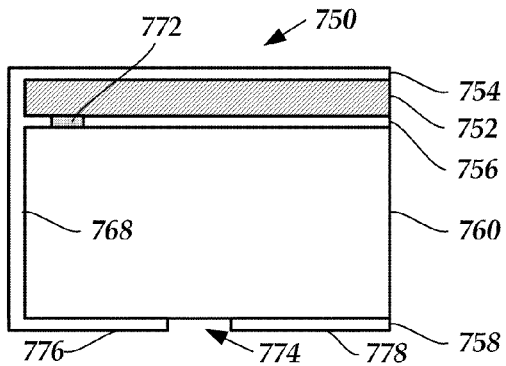
FIGS. 11A and 11B are schematic front and back side views of a further embodiment of a transducer, according to the invention.
Figure 11C:
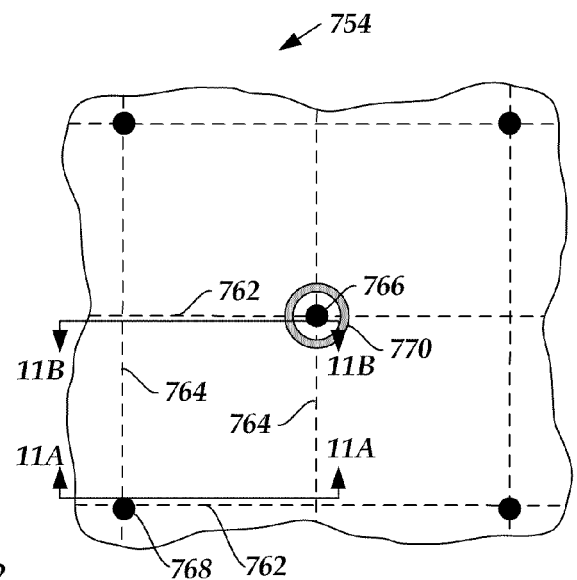
FIGS. 11C, 11D, and 11E are schematic top views of first, second, and third metal layers of the transducer of FIGS. 11A and 11B, also illustrating the arrangement of multiple transducers (separated by the dotted lines), according to the invention.
Figure 11B:
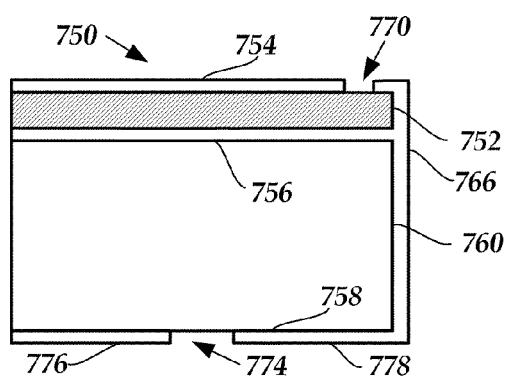
Figure 11D:
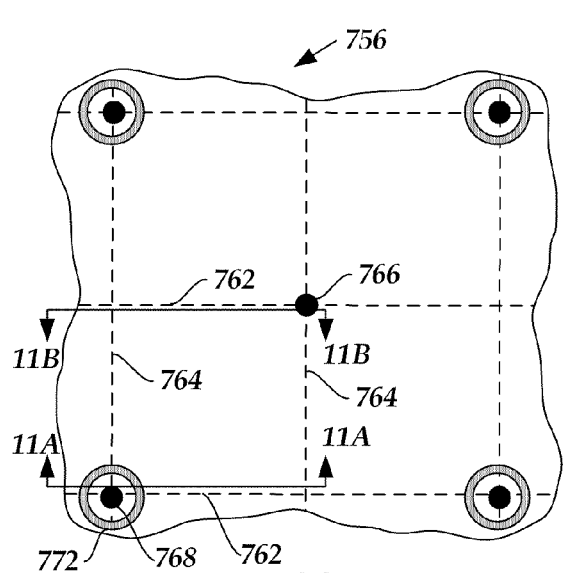
Figure 11E:
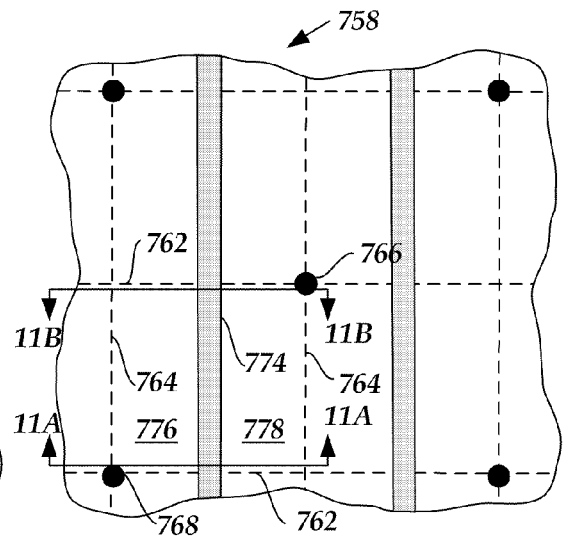

FIGS. 11A-11E illustrate yet another embodiment of a transducer 750. FIGS. 11A and 11B are side views from opposing sides of the transducer. The transducer 750 includes a transducing element 752, a first patterned metal layer 754 (FIG. 11C), a second patterned metal layer 756 (FIG. 11D), a third patterned metal layer 758 (FIG. 11E), and a backing layer 760. FIGS. 11C-11E correspond to the first, second, and third patterned metal layers, respectively, and are illustrated in an arrangement for generating multiple transducers (similar to the arrangements in FIGS. 8 and 9). Each transducer corresponds to one of the rectangular regions bounded by the dotted lines (e.g., lines 762, 764). Any transducer element can be used including, for example, the transducer element 602 of FIG. 6 (although, for this embodiment, the pads 608 are unnecessary and may be omitted or replaced with additional transducing elements.)

In forming this transducer, vias 766, 768 are formed through all of the layers of the transducer and either coated or filled with metal or alloy. When the transducers are separated from each other, each via 766, 768 will be exposed similar to the via 718' in FIG. 10. In addition, a separation 770 is formed around via 766 in the first metal layer 754 and a separation is formed 772 around via 768 in the second metal layer 756. In the third metal layer 758, a separation 774 divides the layer 758 into a first contact 776 and a second contact 778. The respective separations in each metal layer can be formed as each of the metal layers is deposited or the respective separations can be formed by patterning and etching (or otherwise removing a portion of the metal) a previously formed metal layer.

The vias are generally made and coated/filled after forming each of the layers of the transducer. The via 766 couples the majority of second metal layer 756 to the second contact 778. The via 768 couples the majority of the first metal layer 754 to the first contact 776. The wires from the remainder of the electronics of the ultrasound system can be connected to the first and second contacts 776, 778 (see, e.g., FIG. 4). The presence of the backing layer 760 may permit the use of heat-based attachment methods for attaching the wires to the first and second contact 776, 778 by protecting the transducer element 750 from the heat generated by attachment. This embodiment also lends itself to electrical connection via preformed pads in the modular fitting 530 shown in FIG. 5.

FIG. 12 illustrates another arrangement of a transducer 800 with a transducer element 802 comprising piezoelectric regions 804 separated by non-piezoelectric regions 806. The transducer 800 also includes two metal layers 808 and 810; a matching layer 812, and a backing layer 814. The transducer 800 is coupled to the remainder of the device electronics via contact wires 816 and 818 that are disposed next to, or over, a non-piezoelectric region 806'.

FIGS. 13A-13G illustrate one embodiment of a method of making the transducer 800. It will be understood that a variety of other methods can be used to form the transducer 800. A piezoelectric material 804' is removably attached to a carrier 820 using any suitable technique including adhesives, waxes, and the like, as illustrated in FIG. 13A. Cuts are formed in the piezoelectric material 804' to form piezoelectric regions 804, as illustrated in FIG. 13B. The cuts can be formed using any suitable technique including coating the piezoelectric material 804' with a positive or negative photoresist; patterning and developing the photoresist to expose the portions of the piezoelectric material 804' to be removed; and etching the exposed piezoelectric material to form the cuts. Other methods for forming the cuts include, for example, wet chemical etching, reactive ion etching, plasma etching, microdicing, and the like. After the cuts are formed, the cuts can be filled with a suitable non-piezoelectric material, such as, for example, epoxy, filled adhesive, or the like, to form the non-piezoelectric regions 806, as illustrated in FIG. 13B. Any suitable method for filling the cuts can be used including, for example, spin coating, dip coating, silkscreening, and the like. At least one of the non-piezoelectric regions 806' is formed for later use in coupling a wire 816 to the metal layer 808 over that region (see FIG. 12) and may be larger than other non-piezoelectric regions.

The exposed surface of the piezoelectric regions 804 and non-piezoelectric regions 806 is metallized to generate metal layer 810, as illustrated in FIG. 13C. The metallization can be performed using any suitable technique including, but not limited to, electroplating, electroless plating, sputtering, chemical or physical vapor deposition, and the like.

A backing layer 814 is formed over the metal layer 810, as illustrated in FIG. 13D. The backing layer can be formed using any suitable technique including casting, chemical or physical vapor deposition, coating (e.g., spin coating, dip coating, sputtering), and the like. The backing layer is typically formed using a non-conductive material and preferably is used to acoustically match the piezoelectric material.

The carrier layer 820 is removed, as illustrated in FIG. 13E. A second metal layer 808 is formed over the exposed at least a portion of the exposed surface of the piezoelectric regions 804 and non-piezoelectric regions 806, as illustrated in FIG. 13F. The metallization can be performed using any suitable technique including, but not limited to, electroplating, electroless plating, sputtering, chemical or physical vapor deposition, and the like. A portion 822 of the exposed surface of the piezoelectric regions 804 may be left exposed by masking the portion of the surface prior to form the metal layer 808. Alternatively or additionally, the portion 822 of the exposed surface of the piezoelectric regions 804 may be exposed after forming the metal layer 808 by patterning and etching the metal layer using, for example, a positive or negative photoresist.

The exposed portion 822 of the piezoelectric region 804 can be removed using an suitable technique, for example, selective etching the of the piezoelectric material 804, to expose a portion of the underlying metal layer 810, as illustrated in FIG. 13G. A matching layer 812 is disposed over the metal layer 808 and, optionally, over the exposed portion of the metal layer 810, as also illustrated in FIG. 13G. The matching layer can be formed by any suitable technique including, but not limited to, casting, chemical or physical vapor deposition, coating (e.g., spin coating, dip coating, sputtering), and the like. The matching layer is typically formed using a non-conductive material and is used to acoustically match the piezoelectric material.

A portion of the matching layer 812 is removed to exposed portions of the metal layer 808 and 810 to allow for attachment of wires 816 and 818, as illustrated in FIG. 12. It should be noted that the wires 816 and 818 are not attached to portions of the metal layers 808 and 810 that are directly over or under a piezoelectric region 804. Accordingly, in at least some embodiments, heat-based attachment methods can be used to attach the wires 816 and 818 to the metal layers 808 and 810.

Figure 14A:
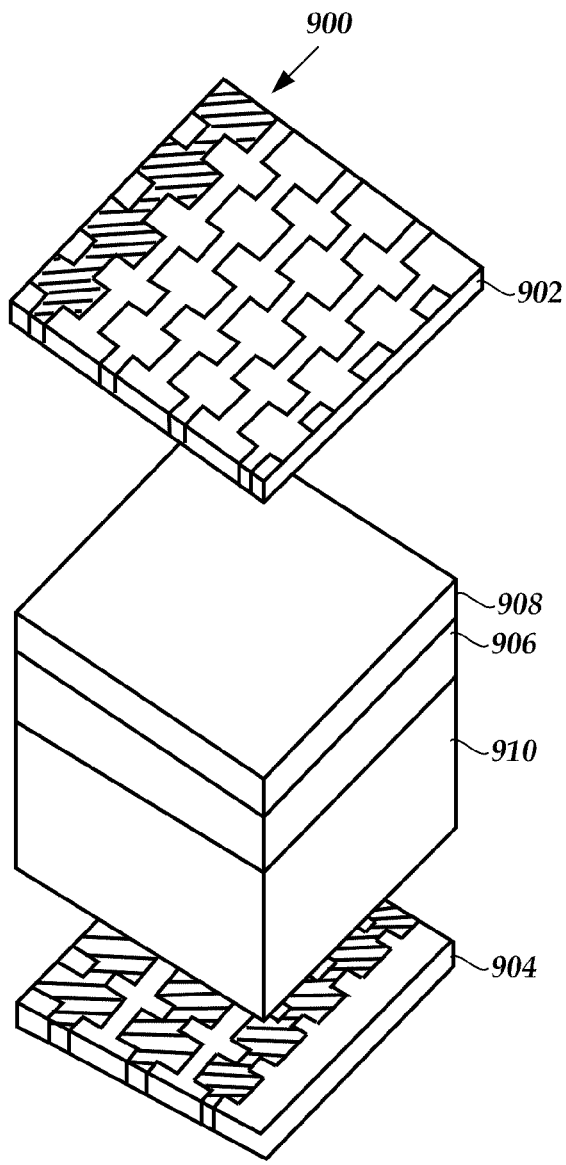
FIG. 14A is a schematic partial exploded view of an arrangement of multiple transducers corresponding to a fifth embodiment according to the invention.
Figure 14B:
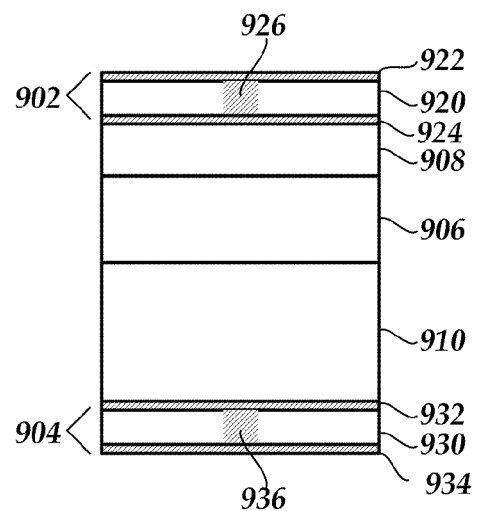
FIGS. 14B and 14C are schematic front and side views of the transducer of FIG. 14A, according to the invention.
Figure 14C:
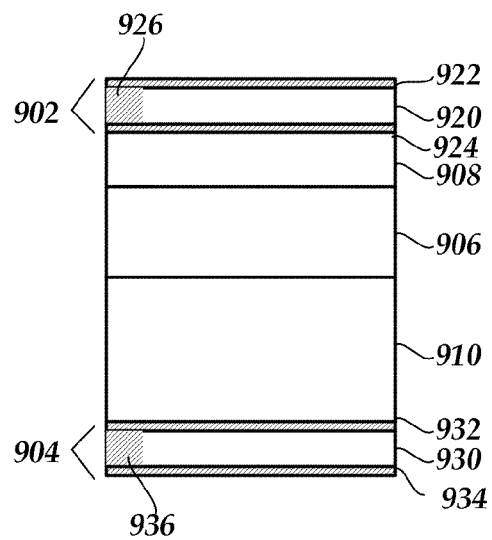

FIGS. 14A-14C illustrate another transducer 900 with top and bottom flexible circuit layers 902, 904; a transducer element 906; a matching layer 908; and a backing layer 910

(which may also function as a matching layer). FIG. 14A is a partially exploded view of one embodiment that includes multiple transducers that can be separated along the dotted lines. FIGS. 14B and 14C illustrate side views (taken along two orthogonal sides) of a single transducer.

The transducer element 906 may be a single crystal of piezoelectric material or any other suitable arrangement of piezoelectric material that can form a transducer element (see e.g., the transducer element of FIG. 6 with or without the non-transducing pads). The matching layer 908 and can be formed using any suitable conductive material that is acoustically matched to the piezoelectric material. The backing layer 910 can be formed using any suitable conductive material and may, in at least some embodiments, be acoustically matched to the piezoelectric material of layer 906.

The flexible circuit layers 902, 904 are each formed from a non-conductive carrier substrate 920, 930, respectively, such as polyimide or any other suitable polymeric material, with metal traces 922, 924, 932, 934 formed on the top and bottom of the non-conductive carrier substrate and electrically coupled by at least one metallic via 926, 936 extending through the non-conductive base 920, 930. The metal traces can be made using a single metal or alloy or can be made using layers of metals or alloys. The metal traces can be patterned or may cover an entire surface of the carrier substrate. In one embodiment, the conductive metal traces and vias are formed using copper and the exposed traces are then covered with Ni/Cr and then gold or another metal that is inert under physiological conditions. It will be understood that the via can be positioned anywhere within the flexible circuit layer (e.g., in the middle or along the edge of the flexible circuit layer).

Wires can then be coupled to the flexible circuit layers 902, 904 to electrically connect the transducer to the remaining electronics of the ultrasound system. The flexible circuit, matching layer, and backing layer separate the wires from the transducer element to reduce heating of the transducer element if a heat-based bonding method is used to attach the wires to the transducer.

Figure 15A:
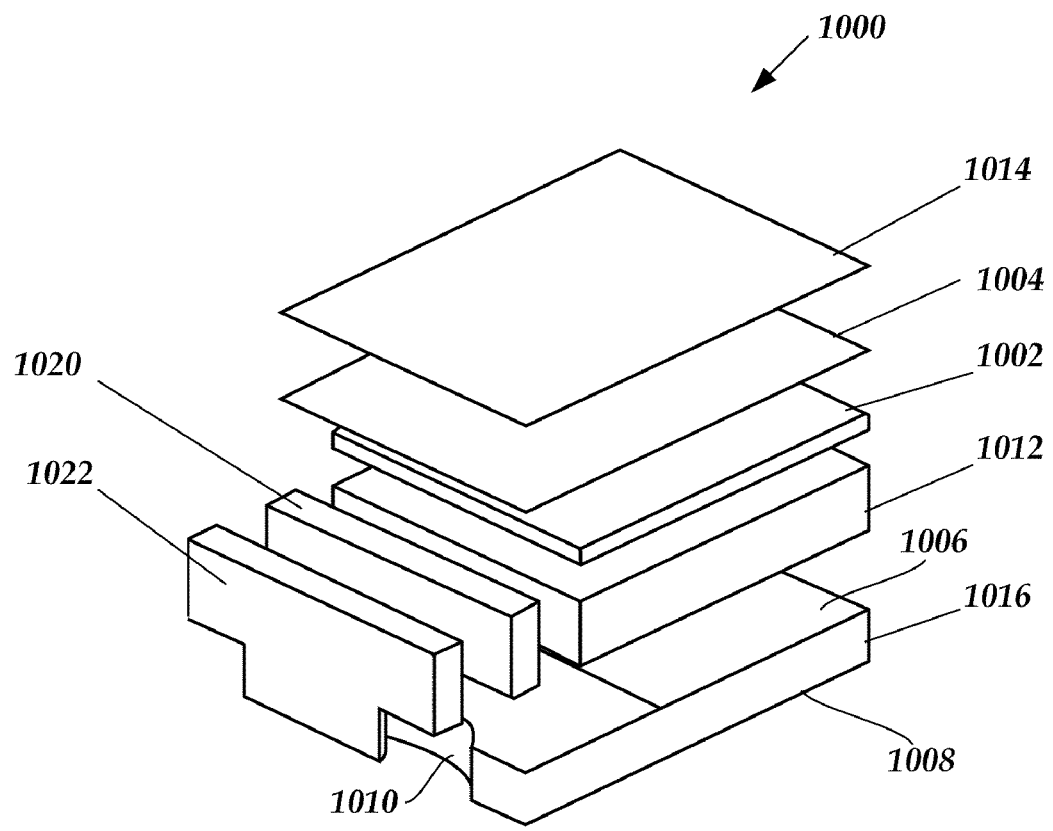
FIG. 15A is a schematic exploded view of a sixth embodiment of a transducer, according to the invention.
Figure 15B:
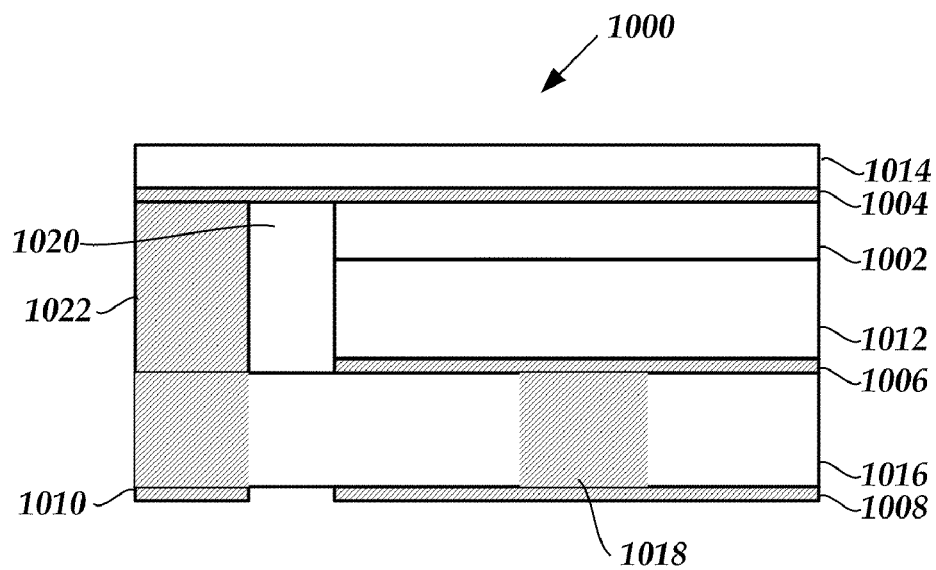
FIG. 15B is a schematic cross-section view of the transducer of FIG. 15A, according to the invention.

FIGS. 15A and 15B illustrate another embodiment of a transducer 1000. This transducer 1000 includes a transducer element 1002; a first metal layer forming separated contacts 1008, 1010; second and third metal layers 1004, 1006; backing layer 1012; matching layer 1014; carrier layer 1016; via 1018; non-conductive wall 1020; and vertical conductor 1022. Any suitable transducer element 1002 can be used including single crystal elements or transducer elements with multiple transducing members (as illustrated, for example, in FIG. 6 with or without the non-transducing pads.)

The backing layer 1012 and matching layer 1014 can be made of the same or different materials. The backing layer 1012 in the illustrated embodiment is conductive. In an alternative embodiment, the matching layer can be disposed between the transducer element 1002 and the third metal layer 1004. In this alternative embodiment, the matching layer 1014 is also conductive.

In at least some embodiments, the carrier layer 1016, metal layer 1006, and contacts 1008, 1010 can be any thin film or thick film circuit material. The carrier layer 1016 can be any suitable non-conductive substrate material including, but not limited to, polymeric materials and ceramic materials. The first metal layer is patterned to form the contacts 1008, 1010. This thick or thin film circuit can be bonded to the backing layer 1012 using any technique including, but not limited to, using conductive adhesive, conductive epoxy, and the like. In one embodiment, the carrier layer 1016, metal layer 1006, and contacts 1008, 1010 are a ceramic thick film circuit.

The contact 1008 is electrically coupled to the metal layer 1006 through the conductive via 1018. The contact 1010 is coupled to the metal layer 1004 through the vertical conductor 1022. The non-conductive wall 1020 insulates the transducer element 1002 from the vertical conductor 1022. The non-conductive wall 1020 and vertical conductor 1022 can be attached to the other components using any suitable technique including, but not limited to, using conductive adhesive, conductive epoxy, and the like. In at least some embodiments, the vertical sidewall of the carrier layer 1016 adjacent to the vertical conductor 1022 is coated with metal to facilitate coupling the vertical conductor 1022 to the contact 1010. Wires to the remainder of the system electronics can be attached to the contact layers 1008, 1010. This embodiment also lends itself to electrical connection via preformed pads in the modular fitting 530 shown in FIG. 5.

Figure 16:
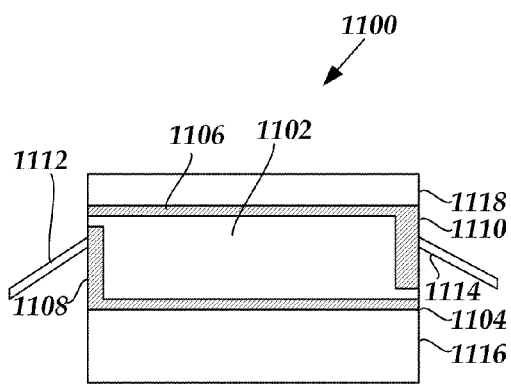
FIG. 16 is a schematic cross-sectional view of a seventh embodiment of a transducer, according to the invention.

FIG. 16 illustrates another embodiment of a transducer 1100. The transducer 1100 includes a transducer element 1102; metal layers 1104, 1106 with corresponding vertical contact pads 1108, 1110 for attachment of wires 1112, 1114; a backing layer 1116; and a matching layer 1118.

Figure 17C:
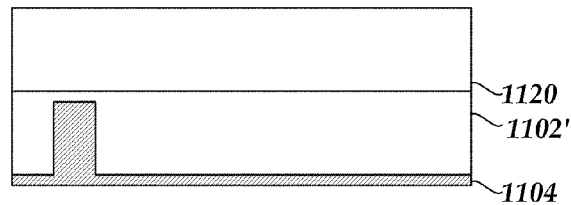
FIGS. 17A-17F are schematic cross-sectional views of steps in one embodiment of a method of making the transducer of FIG. 16, according to the invention.
Figure 17D:
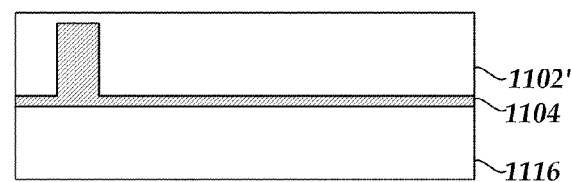
Figure 17A:
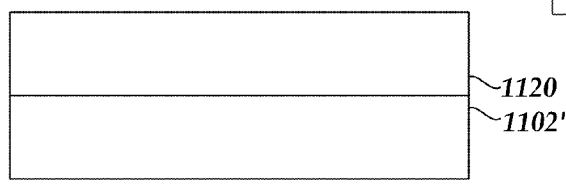
Figure 17E:
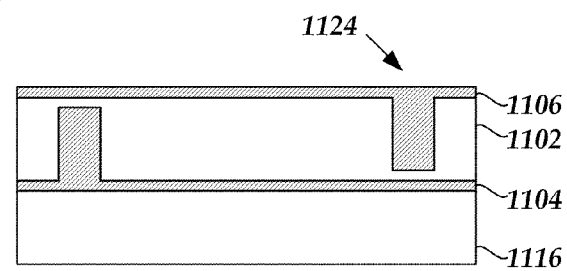
Figure 17B:
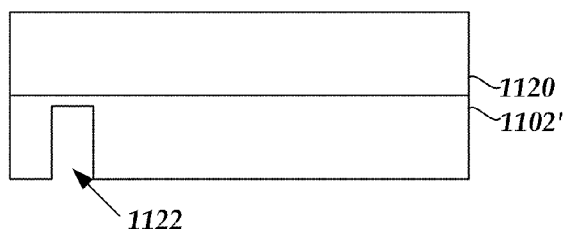

FIGS. 17A-17F illustrate one embodiment of a method of making the transducer 1100. Transducer material 1102' is removably disposed on a carrier 1120, as illustrated in FIG. 17A. A portion of the transducer material 1102' is then removed to form one or more vertical slots 1122, as illustrated in FIG. 17B. Preferably, the vertical slots are between ½ to ¾ the thickness of the transducer material 1102'. For example, the transducer material 1102' can be patterned and etched using a positive or negative photoresist material or the transducer material 1102' can be cut or otherwise diced. A metal layer 1104 is formed over the transducer material 1102' and within the vertical slot(s) 1122, as illustrated in FIG. 17C. The metal layer 1104 can be formed using any suitable method including, but not limited to, electroplating, electroless plating, sputtering, chemical or physical vapor deposition, and the like. Any suitable metal, alloy, or combinations thereof may be used. For example, the metal layer may be formed by plating the surface with Ni/Cr and then with gold. A backing layer 1116 is disposed over the metal layer 1104 and the carrier layer 1120 is removed, as illustrated in FIG. 17D.

Figure 17F:
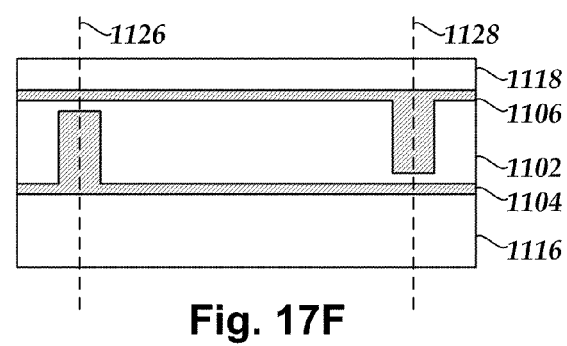

One or more vertical slots 1124 are then formed in the opposite side of the transducer material 1102' and then filled with metal, along with the formation of metal layer 1106, as illustrated in FIG. 17E. Preferably, the vertical slots are between ½ to ¾ the thickness of the transducer material 1102'. As an example, the metal layer may be formed by plating the surface with Ni/Cr and then with gold. A matching layer 1118 is disposed over the metal layer 1106 and the construct is then diced apart along lines 1126, 1128 to expose contact layers 1108, 1110, as illustrated in FIGS. 17F and 16. This embodiment also lends itself to electrical connection via preformed pads in the modular fitting 530 shown in FIG. 5.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An ultrasound transducer, comprising:
   a transducer element comprising a material configured and arranged to convert electrical energy to ultrasound energy, the transducer element further comprising a first non-transducing pad defined in the transducer element;

a first metal layer substantially disposed over a first surface of the transducer element and over the first non-transducing pad, wherein the first non-transducing pad is non-conductive, formed of a heat-resistant material, and configured and arranged to facilitate heat-based attachment of at least one wire to the first metal layer at a position corresponding to the first non-transducing pad; and a second metal layer substantially disposed over a second surface of the transducer element.

2. The ultrasound transducer of claim 1, further comprising a second non-transducing pad defined in the transducer element and a metal pad disposed over the second non-transducing pad and in electrical communication with the second metal layer, wherein the second non-transducing pad is non-conductive.

3. The ultrasound transducer of claim 2, wherein the metal pad is disposed over a portion of the first surface of the transducer element.

4. The ultrasound transducer of claim 3, further comprising a metal via through the transducer element and coupling the metal pad to the second metal layer.

5. The ultrasound transducer of claim 3, wherein the metal pad and the first metal layer are separated by an open separation region.

6. The ultrasound transducer of claim 2, wherein the first and second surfaces are opposing surfaces of the transducer element and a portion of the metal pad is disposed on a third surface of the transducer element, wherein the third surface is between the first and second surfaces.

7. The ultrasound transducer of claim 1, wherein the first metal layer extends beyond the transducer element to provide a contact pad configured and arranged for coupling of a wire to the first metal layer and the second metal layer comprises a portion disposed over the first non-transducing pad and configured and arrange for coupling of a wire to the second metal layer.

8. The ultrasound transducer of claim 1, wherein the first metal layer extends beyond the transducer element to provide a contact pad configured and arranged for coupling of a first contact on a modular fitting of a catheter to the first metal layer and the second metal layer comprises a portion disposed over the first non-transducing pad and configured and arrange for coupling of a second contact on the modular fitting of the catheter to the second metal layer.

9. A catheter assembly for an intravascular ultrasound system, the catheter assembly comprising:
  a catheter having a longitudinal length, a distal end, and a proximal end, the catheter comprising a lumen extending along the longitudinal length of the catheter from the proximal end to the distal end; and
  an imaging core configured and arranged for inserting into the lumen, the imaging core comprising
    a rotatable driveshaft having a distal end and a longitudinal length,
    the transducer of claim 1 mounted to the distal end of the rotatable driveshaft, the transducer configured and arranged for transforming applied electrical pulses to acoustic pulses and also for transforming received echo pulses to electrical pulses, and
    a twisted wire cable, the twisted wire cable comprising i) two wires running along the cable and electrically coupled to respective contacts of the transducer, and ii) a shield extending along the cable and within which a portion of the two wires are disposed.

10. An ultrasound transducer, comprising:
  a transducer element comprising a material configured and arranged to convert electrical energy to ultrasound energy;
  a first metal layer substantially disposed over a first surface of the transducer element;
  a second metal layer substantially disposed over a second surface of the transducer element, wherein the second surface opposes the first surface;
  a backing layer disposed over the second metal layer; and
  a third metal layer disposed over the backing layer, the third metal layer defining a first contact and a second contact that are separated from each other;
  wherein the first contact is coupled to the first metal layer by a first contact via and the second contact is coupled to the second metal layer by a second contact via.

11. The ultrasound transducer of claim 10, wherein the first metal via is disposed-along at least a portion of an edge of the transducer element and the backing layer.

12. The ultrasound transducer of claim 11, wherein the second metal via is disposed along at least a portion of any edge of the backing layer.

13. The ultrasound transducer of claim 11, wherein the second metal via is disposed also along at least a portion of an edge of the transducer element.

14. An ultrasound transducer, comprising:
  a transducer element comprising a material configured and arranged to convert electrical energy to ultrasound energy;
  a first thin film circuit comprising a first substrate with metal traces disposed on opposing sides of the first substrate and electrically coupled together, wherein the metal traces of the first thin film circuit are configured and arranged to provide a contact pad on one side of the first substrate and an electrode for providing electrical signals to the transducer element on another side of the first substrate; and
  a second thin film circuit comprising a second substrate with metal traces disposed on opposing sides of the second substrate and electrically coupled together, wherein the metal traces of the second thin film circuit are configured and arranged to provide a contact pad on one side of the second substrate and an electrode for providing electrical signals to the transducer element on another side of the second substrate;
  wherein the transducer element is disposed between the first and second thin film circuits.

15. The ultrasound transducer of claim 14, further comprising a conductive matching layer disposed between the transducer element and the first thin film circuit.

16. The ultrasound transducer of claim 15, further comprising a conductive backing layer disposed between the transducer element and the second thin film circuit.

17. An ultrasound transducer, comprising:
  a transducer element comprising a material configured and arranged to convert electrical energy to ultrasound energy;
  a carrier substrate comprising a first surface and a second surface opposing the first surface;
  a first metal layer disposed on the first surface of the carrier substrate, the first metal layer defining a first contact and a second contact that are separate from each other;
  a second metal layer disposed on the second surface of the carrier substrate and in electrical communication with the second contact on the first surface of the carrier substrate;
  a third metal layer, wherein the transducer element is disposed between the second metal layer and the third metal layer; and a conducting structure electrically coupling the first contact with the third metal layer, wherein the conducting structure itself is electrically insulated from the transducer element.

18. The ultrasound transducer of claim 17, wherein the carrier substrate, first metal layer, and second metal layer are a thick film circuit.

19. The ultrasound transducer of claim 17, further comprising a conductive via through the carrier substrate and electrically coupling the second contact to the second metal layer.

20. An ultrasound transducer, comprising:
a transducer element comprising a material configured and arranged to convert electrical energy to ultrasound energy, the transducer element further comprising a first surface, a second surface opposing the first surface, and an edge surface between the first and second surfaces;
a first metal layer disposed over the first surface of the transducer element;
a second metal layer disposed over the second surface of the transducer element;
a first contact extending from the first metal layer along a first portion of the edge surface of the transducer element; and
a second contact extending from the second metal layer along a second portion of the edge surface of the transducer element.

21. A method of making the ultrasound transducer of claim 20, the method comprising:
forming at least one first vertical slot extending from a first surface partway through a transducer element;
disposing metal within the at least one first vertical slot to at least coat exposed surfaces of the transducer element within the at least one first vertical slot;
disposing a first metal layer over the first surface of the transducer element and in contact with the metal disposed within the at least one first vertical slot;
forming at least one second vertical slot extending from a second surface partway through the transducer element, wherein the second surface of the transducer element opposes the first surface of the transducer element;
disposing metal within the at least one second vertical slot to at least coat exposed surfaces of the transducer element within the at least one second vertical slot;
disposing a second metal layer over the second surface of the transducer element and in contact with the metal disposed within the at least one second vertical slot; and
cutting the transducer element through the first and second vertical slots to form the ultrasound transducer with the first and second contacts formed from the metal disposed in the first and second vertical slots, respectively, wherein the first and second contacts are disposed on the first and second portions of the edge surface of the transducer element.

22. The method of claim 21, further comprising disposing a matching layer over the second metal layer.

23. The method of claim 21, further comprising disposing a backing layer over the first metal layer.

* * * * *